United States Patent [19]

Sugimoto et al.

[11] 4,426,383
[45] Jan. 17, 1984

[54] THEOPHYLLINE AND THEOBROMINE DERIVATIVES

[75] Inventors: Hachiro Sugimoto, Kawaguchi; Takaharu Nakamura, Abiko; Sachiyuki Hamazo, Tokyo; Toshiji Igarashi, Saitama; Yoshiharu Daiku, Tokyo, all of Japan

[73] Assignee: Eisai Co., Ltd., Tokyo, Japan

[21] Appl. No.: 298,227

[22] Filed: Aug. 31, 1981

[30] Foreign Application Priority Data

Sep. 4, 1980 [JP] Japan .............................. 55-121712
Sep. 4, 1980 [JP] Japan .............................. 55-121713

[51] Int. Cl.³ ................ C07D 473/08; C07D 473/10; A61K 31/52
[52] U.S. Cl. .................... 424/253; 544/267; 424/250
[58] Field of Search ............. 424/250, 251, 253; 544/267, 268, 269

[56] References Cited

U.S. PATENT DOCUMENTS 3,459,753  8/1969  Boltze et al. .................... 424/253
4,284,633  8/1981  Friebe et al. .................... 544/267

FOREIGN PATENT DOCUMENTS 23350  2/1981  European Pat. Off. .

*Primary Examiner*—Nicholas S. Rizzo
*Attorney, Agent, or Firm*—Flynn, Thiel, Boutell & Tanis

[57] ABSTRACT

A novel compound has the following formula:

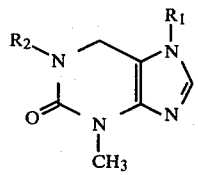

[I]

in which $R_1$ and $R_2$ are methyl or a group having the formula:

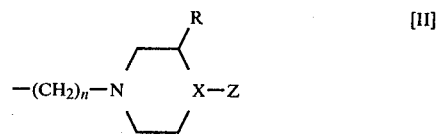

[II]

provided that one of $R_1$ and $R_2$ is methyl and the other is said group, wherein R stands for a hydrogen atom or a lower alkyl group, Z stands for a group

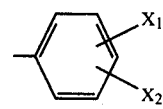

in which $X_1$ and $X_2$, which may be the same or different, stand for a hydrogen atom, a lower alkyl group, a lower alkoxy group, a trifluoromethyl group or a halogen atom, or a pyridyl group or a group

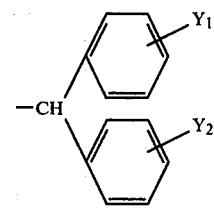

in which $Y_1$ and $Y_2$, which may be the same or different stand for a hydrogen atom, a lower alkyl group, a lower alkoxy group, a trifluoromethyl group or a halogen atom, X stands for a nitrogen or carbon atom, and n is an integer of from 2 to 10, provided that when $R_2$ is the group having the formula II, X is not carbon and Z is not pyridyl.

15 Claims, No Drawings

THEOPHYLLINE AND THEOBROMINE DERIVATIVES

The present invention relates to a theophylline derivative and a theobromine derivative and then processes for manufacturing them. These compounds are novel and have excellent medicinal actions.

More particularly, the theophylline and theobromine derivatives have the following formula.

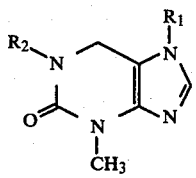

in which $R_1$ and $R_2$ are methyl or a group having the formula:

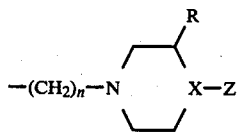

provided that one of $R_1$ and $R_2$ is methyl and the other is said group, wherein R stands for a hydrogen atom or a lower alkyl group, Z stands for a group

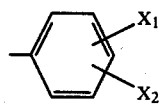

in which $X_1$ and $X_2$, which may be the same or different, stand for a hydrogen atom, a lower alkyl group, a lower alkoxy group, a trifluoromethyl group or a halogen atom, or a pyridyl group or a group

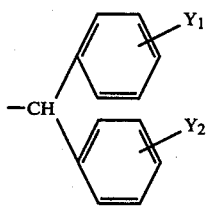

in which $Y_1$ and $Y_2$, which may be the same or different stand for a hydrogen atom, a lower alkyl group, a lower alkoxy group, a trifluoromethyl group or a halogen atom, X stands for a nitrogen or carbon atom, and n is an integer of from 2 to 10, provided that when $R_2$ is the group having the formula II, X is not carbon and Z is not pyridyl.

The invention includes an acid addition salt of the derivatives defined as above as well.

Among the compounds according to the invention, the theophylline derivatives have the following formula III:

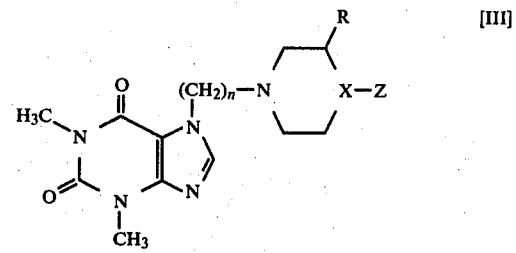

wherein R stands for a hydrogen atom or a lower alkyl group, Z stands for a group

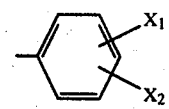

in which $X_1$ and $X_2$, which may be the same or different, stand for a hydrogen atom, a lower alkyl group, a lower alkoxy group, a trifluoromethyl group or a halogen atom, or a pyridyl group or a group

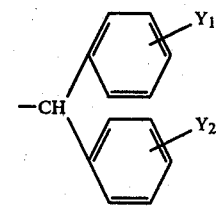

in which $Y_1$ and $Y_2$, which may be the same or different stand for a hydrogen atom, a lower alkyl group, a lower alkoxy group, a trifluoromethyl group or a halogen atom, X stands for a nitrogen or carbon atom, and n is an integer of from 2 to 10.

Then, the theobromine derivatives have the following formula IV:

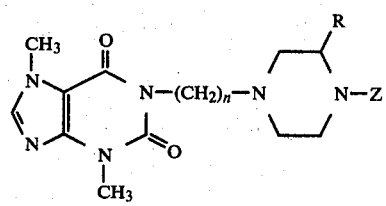

wherein R stands for a hydrogen atom or a lower alkyl group, Z stands for a group

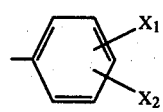

in which $X_1$ and $X_2$, which may be the same or different, stand for a hydrogen atom, a lower alkyl group, a lower alkoxy group, a trifluoromethyl group or a halogen atom, or a group

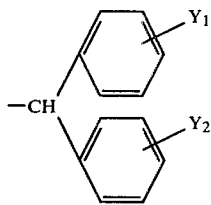

in which $Y_1$ and $Y_2$, which may be the same or different, stand for a hydrogen atom, a lower alkyl group, a lower alkoxy group, a trifluoromethyl group or a halogen atom, and n is an integer of from 2 to 10.

In the definitions of R, $X_1$, $X_2$, $Y_1$ and $Y_2$ of the general formula [I], by the term "lower alkyl group" are meant linear or branched alkyl groups having 1 to 6 carbon atoms, such as methyl, ethyl, n-propyl, isopropyl, isobutyl, 1-methylpropyl, tert-butyl, n-pentyl, 1-ethylpropyl, isoamyl and n-hexyl groups. By the term "lower alkoxy group" are meant alkoxy groups corresponding to the above-mentioned lower alkyl groups. As the halogen atom, there can be mentioned chlorine, bromine, iodine and fluorine.

Among the theobromine derivatives defined as before, those having the formula IV in which Z is

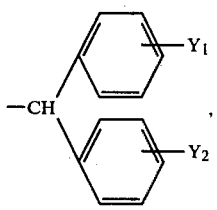

or Z is

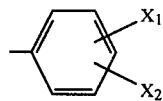

and n is 2,9 or 10 is preferable.

The compound [I] of the present invention can easily be converted to an acid addition salt by reaction with a pharmacologically acceptable inorganic or organic acid. As the inorganic acid, there can be mentioned hydrochloric acid, hydrobromic acid, hydroiodic acid and sulfuric acid, and as the organic acid, there can be mentioned maleic acid, fumaric acid, succinic acid, acetic acid, malonic acid, citric acid and benzoic acid.

Typical examples of the theophilline derivatives of the invention will now be mentioned, though the scope of the present invention is not limited by these examples.

7-{2-[4-p-chlorobenzhydrylpiperazinyl-(1)]ethyl}-theophylline
7-{3-[4-p-chlorobenzhydrylpiperazinyl-(1)]-n-propyl}-theophylline
7-{4-[4-p-chlorobenzhydrylpiperazinyl-(1)]-n-butyl}-theophylline
7-{5-[4-p-methylbenzhydrylpiperazinyl-(1)]-n-pentyl}-theophylline
7-{6-[4-p-methoxybenzhydrylpiperazinyl-(1)]-n-hexyl}-theophylline
7-{7-[4-o-trifluoromethylbenzhydrylpiperazinyl-(1)]-n-heptyl}-theophylline
7-{8-[4-benzhydrylpiperazinyl-(1)]-n-octyl}-theophylline
7-{9-[4-p-chlorobenzhydrylpiperazinyl-(1)]-n-nonyl}-theophylline
7-{10-[4-p-ethoxybenzhydrylpiperazinyl-(1)]-n-decyl}-theophylline
7-{4-[4-(4',4''-dichlorodiphenylmethyl)piperazinyl-(1)]-n-butyl}-theophylline
7-{2-[(4-phenyl)piperazinyl-(1)]ethyl}-theophyllin
7-{3-[(4-phenyl)piperazinyl-(1)]-n-propyl}-theophylline
7-{4-[(4-phenyl)piperazinyl-(1)]-n-butyl}-theophylline
7-{-5-[(4-phenyl)piperazinyl-(1)]-n-pentyl}-theophylline
7-{6-[(4-phenyl)piperazinyl-(1)]-n-hexyl}-theophylline
7-{2-[4-o-methylphenylpiperazinyl-(1)]-ethyl}-theophylline
7-{3-[4-o-methylphenylpiperazinyl-(1)]-n-propyl}-theophylline
7-{5-[4-o-methylphenylpiperazinyl-(1)]-n-pentyl}-theophylline
7-{2-[4-m-methylphenylpiperazinyl-(1)]-ethyl}-theophylline
7-{4-[4-m-methylphenylpiperazinyl-(1)]-n-butyl}-theophylline
7-{5-[4-m-methylphenylpiperazinyl-(1)]-n-pentyl}-theophylline
7-{6-[4-m-methylphenylpiperazinyl-(1)]-n-hexyl}-theophylline
7-{2-[4-(2,3-dimethylphenyl)piperazinyl-(1)]-ethyl}-theophylline
7-{2-[4-(2,6-dimethylphenyl)piperazinyl-(1)]-ethyl}-theophylline
7-{2-[4-(2,6-dimethylphenyl)piperazinyl-(1)]-n-propyl}-theophylline
7-{4-[4-(2,6-dimethylphenyl)piperazinyl-(1)]-n-butyl}-theophylline
7-{5-[4-(2,6-dimethylphenyl)piperazinyl-(1)]-n-pentyl}-theophylline
7-{6-[4-(2,6-dimethylphenyl)piperazinyl-(1)]-n-hexyl}-theophylline
7-{3-[4-(2,3-dimethylphenyl)piperazinyl-(1)]-n-propyl}-theophylline
7-{4-[4-(2,3-dimethylphenyl)piperazinyl-(1)]-n-butyl}-theophylline
7-{5-[4-(2,3-dimethylphenyl)piperazinyl-(1)]-n-pentyl}-theophylline
7-{6-[4-(2,3-dimethylphenyl)piperazinyl-(1)]-n-hexyl}-theophylline
7-{2-[4-(2,5-dimethylphenyl)piperazinyl-(1)]-ethyl}-theophylline
7-{3-[4-(2,5-dimethylphenyl)piperazinyl-(1)]-n-propyl}-theophylline
7-{4-[4-(2,5-dimethylphenyl)piperazinyl-(1)]-n-butyl}-theophylline
7-{5-[4-(2,5-dimethylphenyl)piperazinyl-(1)]-n-pentyl}-theophylline
7-{6-[4-(2,5-dimethylphenyl)piperazinyl-(1)]-n-hexyl}-theophylline
7-{2-[4-o-methoxyphenylpiperazinyl-(1)]-ethyl}-theophylline
7-{3-[4-o-methoxyphenylpiperazinyl-(1)]-n-propyl}-theophylline
7-{4-[4-o-methoxyphenylpiperazinyl-(1)]-n-butyl}-theophylline
7-{5-[4-o-methoxyphenylpiperazinyl-(1)]-n-pentyl}-theophylline 7-{6-[4-o-methoxyphenylpiperazinyl-(1)]-n-hexyl}-theophylline
7-{2-[4-m-methoxyphenylpiperazinyl-(1)]-ethyl}-theophylline
7-{3-[4-m-methoxyphenylpiperazinyl-(1)]-n-propyl}-theophylline
7-{4-[4-m-methoxyphenylpiperazinyl-(1)]-n-butyl}-theophylline
7-{5-[4-m-methoxyphenylpiperazinyl-(1)]-n-pentyl}-theophylline
7-{6-[4-m-methoxyphenylpiperazinyl-(1)]-n-hexyl}-theophylline
7-{2-[4-p-methoxyphenylpiperazinyl-(1)]-ethyl}-theophylline
7-{4-[4-p-methoxyphenylpiperazinyl-(1)]-n-butyl}-theophylline
7-{5-[4-p-methoxyphenylpiperazinyl-(1)]-n-pentyl}-theophylline
7-{-6-[4-p-methoxyphenylpiperazinyl-(1)]-n-hexyl}-theophylline
7-{2-[4-o-chlorophenylpiperazinyl-(1)]-ethyl}-theophylline
7-{4-[4-o-chlorophenylpiperazinyl-(1)]-n-butyl}-theophylline
7-{5-[4-o-chlorophenylpiperazinyl-(1)]-n-pentyl}-theophylline
7-{6-[4-o-chlorophenylpiperazinyl-(1)]-n-hexyl}-theophylline
7-{2-[4-m-chlorophenylpiperazinyl-(1)]-ethyl}-theophylline
7-{4-[4-m-chlorophenylpiperazinyl-(1)]-n-butyl}-theophylline
7-{4-[4-m-chlorophenylpiperazinyl-(1)]-n-pentyl}-theophylline
7-{2-[4-o-chlorophenylpiperazinyl-(1)]-ethyl}-theophylline
7-{4-[4-o-chlorophenylpiperazinyl-(1)]-n-butyl}-theophylline
7-{5-[4-o-chlorophenylpiperazinyl-(1)]-n-pentyl}-theophylline
7-{6-[4-o-chlorophenylpiperazinyl-(1)]-n-hexyl}-theophylline
7-{2-[4-(3,4-dichlorophenyl)piperazinyl-(1)]-ethyl}-theophylline
7-{3-[4-(3,4-dichlorophenyl)piperazinyl-(1)]-n-propyl}-theophylline
7-{4-[4-(3,4-dichlorophenyl)piperazinyl-(1)]-n-butyl}-theophylline
7-{4-[4-p-fluorophenylpiperazinyl-(1)]-n-propyl}-theophylline
7-{5-[4-p-fluorophenylpiperazinyl-(1)]-n-butyl}-theophylline
7-{3-[4-m-trifluoromethylphenylpiperazinyl-(1)]-n-propyl}-theophylline
7-{4-[4-m-trifluoromethylphenylpiperazinyl-(1)]-n-butyl}-theophylline
7-{5-[4-m-trifluoromethylphenylpiperazinyl-(1)]-n-pentyl}-theophylline
7-{4-[4-o-trifluoromethylphenylpiperazinyl-(1)]-n-butyl}-theophylline
7-{3-[4-p-trifluoromethylphenylpiperazinyl-(1)]-n-propyl}-theophylline
7-{2-[4-(2-pyridyl)piperazinyl-(1)]-ethyl}-theophylline
7-{3-[4-(2-pyridyl)piperazinyl-(1)]-n-propyl}-theophylline
7-{4-[4-(2-pyridyl)piperazinyl-(1)]-n-butyl}-theophylline
7-{5-[4-(2-pyridyl)piperazinyl-(1)]-n-pentyl}-theophylline
7-{6-[4-(2-pyridyl)piperazinyl-(1)]-n-hexyl}-theophylline
7-{7-[(3-methyl-4-m-methylphenyl)piperazinyl-(1)]-n-heptyl}-theophylline
7-{2-[(3-methyl-4-phenyl)piperazinyl-(1)]-ethyl}-theophylline
7-{4-[(3-methyl-4-phenyl)piperazinyl-(1)]-n-butyl}-theophylline
7-{5-[(3-methyl-4-phenyl)piperazinyl-(1)]-n-pentyl}-theophylline
7-{2-[(3-methyl-4-p-methoxyphenyl)piperazinyl-(1)]-ethyl}-theophylline
7-{5-[(3-methyl-4-p-methoxyphenyl)piperazinyl-(1)]-n-pentyl}-theophylline
7-{6-[(3-ethyl-4-p-methoxyphenyl)piperazinyl-(1)]-n-hexyl}-theophylline
7-{7-[4-m-chlorophenylpiperazinyl-(1)]-n-heptyl}-theophylline
7-{8-[4-(3,4-dimethylphenyl)piperazinyl-(1)]-n-octyl}-theophylline
7-{9-[4-(2,3-diethylphenyl)piperazinyl-(1)]-n-nonyl}-theophylline
7-{10-[4-m-ethoxyphenylpiperazinyl-(1)-n-decyl}-theophylline
7-{7-[4-(2,3-dimethylphenyl)piperazinyl-(1)]-n-heptyl}-theophylline
7-{7-[4-(2-methyl-3-ethylphenyl)piperazinyl-(1)]-n-heptyl}-theophylline
7-{3-[4-(2-methyl-3-n-propylphenyl)piperazinyl-(1)]-n-propyl}-theophylline
7-{2-[(4-phenyl)piperidinyl]-ethyl}-theophylline
7-{3-[(4-phenyl)piperidinyl]-n-propyl}-theophylline
7-{4-[(4-phenyl)piperidinyl]-n-butyl}-theophylline
7-{5-[(4-p-chlorophenyl)piperidinyl]-n-pentyl}-theophylline
7-{5-[4-(3,4-dichlorophenyl)piperazinyl-(1)]-n-pentyl}-theophylline
7-{7-[4-(2-methyl-5-chlorophenyl)piperazinyl-(1)]-n-heptyl}-theophylline
7-{1-[(4-o-methoxyphenyl)piperazinyl-(1)]-n-decyl}-theophylline
7-{10-[4-(2-methyl-5-chlorophenyl)piperazinyl-(1)]-n-decyl}-theophylline
7-{10-[3-methyl-4-m-methylphenylpiperazinyl-(1)]-n-decyl}-theophylline
7-{10-[4-(3,4-dimethylphenyl)piperazinyl-(1)]-n-decyl}-theophylline.

Theophylline derivatives provided according to the present invention are novel compounds which have not been introduced in any of literature references. They have very high vasolidating and blood flow-increasing actions and they are effective for improving blood flows in the cerebral and coronary arteries and the capillary vessels. Furthermore, the compounds of the present invention have an action of controlling coagulation of blood platelets. Accordingly, they are suitable as agents for remedy of various diseases caused by troubles in blood flows in capillary vessels, cerebral blood vessel disorders and sequelae thereof, stenocardia and cardiac infraction. Moreover, theophylline derivatives provided according to the present invention are excellent in other various pharmacological actions such as the action to the central nervous system, the anti-histaminic action, the analgesic action, the anti-asthmatic action and the hypotensive action. Accordingly, the compounds of the present invention can effectively be used as psychic energizers, anti-histaminic agents, analgesic agents, anti-asthmatic agents and hypotensive agents.

Compounds [III] of the present invention can be prepared according to various processes. For example, a process represented by the following reaction formula is ordinarily adopted:

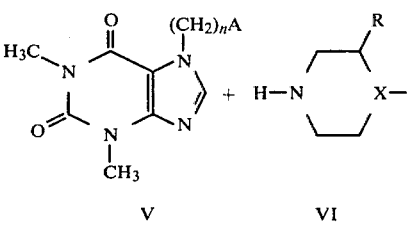

V      VI

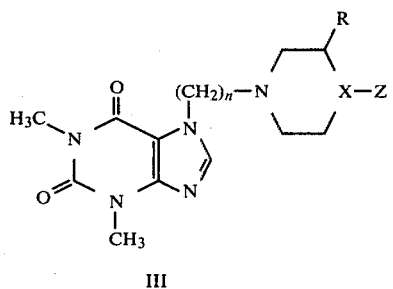

III wherein A stands for a halogen atom or a p-toluenesulfonyloxy group, and R, X, Z and n are as defined above.

In short, a compound III of the present invention can be obtained by reacting a compound represented by the general formula V with a compound represented by the general formula VI.

This reaction is carried out in the absence of a solvent or in the presence of a solvent not participating in the reaction, which is appropriately selected from lower alcohols such as methanol, ethanol, propanol and isopropanol, benzene type solvents such as benzene, toluene and xylene, and ethers such as ethyl ether and tetrahydrofuran. The reaction can be advanced even at room temperature, but it is preferred that the reaction be carried out at an elevated temperature of up to the boiling point of the solvent. The reaction can be performed more smoothly by adding an acid binder such as triethylamine, an alkali metal bicarbonate, an alkali metal carbonate or pyridine to the reaction mixture.

Typical examples of the theobromine derivatives of the invention will now be mentioned, though the scope of the present invention is not limited by these examples.

1-{7-[4-o-methoxyphenylpiperazinyl-(1)]-n-heptyl}-theobromine
1-{6-[4-o-methoxyphenylpiperazinyl-(1)]-n-hexyl}-theobromine
1-{5-[4-m-methoxyphenylpiperazinyl-(1)]-n-pentyl}-theobromine
1-{6-[4-m-methoxyphenylpiperazinyl-(1)]-n-hexyl]-theobromine
1-{8-[4-o-methoxyphenylpiperazinyl-(1)]-n-octyl}-theobromine
1-{10-[4-m-methoxyphenylpiperazinyl-(1)]-n-decyl}-theobromine
1-{2-[4-p-methoxyphenylpiperazinyl-(1)]-ethyl}-theobromine
1-{4-[4-o-ethoxyphenylpiperazinyl-(1)]-n-butyl}-theobromine
1-{4-[4-o,m-dimethylphenylpiperazinyl-(1)]-n-butyl}-theobromine
1-{2-[4-(2,6-dimethylphenylpiperazinyl-(1]ethyl}-theobromine
1-{3-[4-(2,6-dimethylphenyl)piperazinyl-(1)]-n-propyl}-theobromine
1-{4-[4-(2,6-dimethylphenyl)piperazinyl-(1)]-n-butyl}-theobromine
1-{5-[4-(2,6-dimethylphenyl)piperazinyl-(1)]-n-pentyl}-theobromine
1-{2-[4-(2,3-dimethylphenyl)piperazinyl-(1)]-ethyl}-theobromine
1-{3-[4-(2,3-dimethylphenyl)piperazinyl-(1)]n-propyl}-theobromine
1-{4-[4-(2,3-dimethylphenyl)piperazinyl-(1)]-n-butyl}-theobromine
1-{5-[4-(2,3-dimethylphenyl)piperazinyl-(1)]-n-pentyl}-theobromine
1-{6-[4-(2,3-dimethylphenyl)piperazinyl-(1)]-n-hexyl}-theobromine
1-{2-[4-(2,5-dimethylphenyl)piperazinyl-(1)]-ethyl}-theobromine
1-{3-[4-(2,5-dimethylphenyl)piperazinyl-(1)]-n-propyl}-theobromine
1-{4-[4-(2,5-dimethylphenyl)piperazinyl-(1)]-n-butyl}-theobromine
1-{5-[4-(2,5-dimethylphenyl)piperazinyl-(1)]-n-pentyl}-theobromine
1-{6-[4-(2,5-dimethylphenyl)piperazinyl-(1)]-n-hexyl}-theobromine
1-{7-[4-(2,5-dimethylphenyl)piperazinyl-(1)]-n-heptyl}-theobromine
1-{8-[4-(2,3-dimethylphenyl)piperazinyl-(1)]-n-octyl}-theobromine
1-{9-[4-(2,6-dimethylphenyl)piperazinyl-(1)]-n-nonyl}-theobromine
1-{10-[4-(2,5-dimethylphenyl)piperazinyl-(1)]-n-decyl}-theobromine
1-{5-[4-benzhydrylpiperazinyl-(1)]-n-pentyl}-theobromine
1-{2-[4-benzhydrylpiperazinyl-(1)]-ethyl}-theobromine
1-{3-[4-benzhydrylpiperazinyl-(1)]-n-propyl}-theobromine
1-{4-[4-benzhydrylpiperazinyl-(1)]-n-pentyl}-theobromine
1-{5-[4-benzhydrylpiperazinyl-(1)]-n-pentyl}-theobromine
1-{6-[4-benzhydrylpiperazinyl-(1)]-n-hexyl}-theobromine
1-{2-[4-p-chlorobenzhydrylpiperazinyl-(1)]-ethyl}-theobromine
1-{3-[4-p-chlorobenzhydrylpiperazinyl-(1)]-n-propyl}-theobromine
1-{4-[4-p-chlorobenzhydrylpiperazinyl-(1)]-n-butyl}-theobromine
1-{5-[4-p-chlorobenzhydrylpiperazinyl-(1)]-n-pentyl}-theobromine
1-{6-[4-p-chlorobenzhydrylpiperazinyl-(1)]-n-hexyl}-theobromine
1-{10-[4-p-methoxybenzhydrylpiperazinyl-(1)]-n-decyl}-theobromine
1-{4-[4-(4',4''-dichlorophenylmethyl)piperazinyl-(1)]-n-butyl}-theobromine
1-{9-[4-p-chlorobenzhydrylpiperazinyl-(1)]-n-nonyl}-theobromine
1-{8-[4-p-methylbenzyhydrylpiperazinyl-(1)]-n-octyl}-theobromine 1-{7-[4-trifluoromethylbenzhydrylpiperazinyl-(1)]-n-heptyl}-theobromine
1-{6-[4-o-methylphenylpiperazinyl-(1)]-n-hexyl}-theobromine
1-{2-[4-m-methylphenylpiperazinyl-(1)]-ethyl}-theobromine
1-{3-[4-p-methylphenylpiperazinyl-(1)]-n-propyl}-theobromine
1-{4-[4-m-methylphenylpiperazinyl-(1)]-n-butyl}-theobromine
1-{5-[4-p-methylphenylpiperazinyl-(1)]-n-pentyl}-theobromine
1-{7-[4-p-trifluoromethylpiperazinyl-(1)]-n-heptyl}-theobromine
1-{8-[4-p-ethoxyphenylpiperazinyl-(1)]-n-octyl}-theobromine
1-{2-[4-o-chlorophenylpiperazinyl-(1)]-ethyl}-theobromine
1-{3-[4-p-chlorophenylpiperazinyl-(1)]-n-propyl}-theobromine
1-{4-[4-o-chlorophenylpiperazinyl-(1)]-n-butyl}-theobromine
1-{5-[4-p-chlorophenylpiperazinyl-(1)-n-pentyl}-theobromine
1-{6-[4-m-chlorophenylpiperazinyl-(1)]-n-hexyl}-theobromine
1-{7-[4-p-methoxyphenylpiperazinyl-(1)]-n-heptyl}-theobromine
1-{3-[4-(3,4-dichlorophenyl)piperazinyl-(1)]-n-propyl}-theobromine
1-{4-[4-(3,4-dichlorophenyl)piperazinyl-(1)]-n-butyl}-theobromine
1-{5-[4-(3,4-dichlorophenyl)piperazinyl-(1)]-n-pentyl}-theobromine
1-{6-[4-(2,3-dichlorophenyl)piperazinyl-(1)]-n-hexyl}-theobromine
1-{7-[4-(2,5-dichlorophenyl)piperazinyl-(1)]-n-heptyl}-theobromine
1-{8-[4-(2,6-dichlorophenyl)piperazinyl-(1)]-n-octyl}-theobromine
1-{9-[4-(3,4-dichlorophenyl)piperazinyl-(1)]-n-nonyl}-theobromine
1-{10-[4-(3,4-dichlorophenyl)piperazinyl-(1)]-n-decyl}-theobromine
1-{2-[3-methyl-4-phenylpiperazinyl-(1)]-ethyl}-theobromine
1-{3-[3-methyl-4-phenylpiperazinyl-(1)]-n-propyl}-theobromine
1-{4-[3-methyl-4-phenylpiperazinyl-(1)]-n-butyl}-theobromine
1-{3-[3-methyl-4-phenylpiperazinyl-(1)]-n-pentyl}-theobromine
1-{6-[3-methyl-4-phenylpiperazinyl-(1)]-n-hexyl}-theobromine
1-{2-[3-methyl-4-p-methoxyphenylpiperazinyl-(1)]-ethyl}-theobromine
1-{3-[3-methyl-4-p-methoxyphenylpiperazinyl-(1)]-n-propyl}-theobromine
1-{4-[3-methyl-4-o-methoxyphenylpiperazinyl-(1)]-n-butyl}-theobromine
1-{5-[3-methyl-4-m-methoxyphenylpiperazinyl-(1)]-n-pentyl}-theobromine
1-{7-[4-p-fluorophenylpiperazinyl-(1)]-n-heptyl}-theobromine
1-{10-[3-methyl-4-m-methoxyphenylpiperazinyl-(1)]-n-decyl}-theobromine
1-{10-[4-(2,4-dimethylphenylpiperazinyl-(1)]-n-decyl}-theobromine.

Theobromine derivatives provided according to the present invention are novel compounds which have not been introduced in any of literature references. They have very high vasodilating and blood flow-increasing actions and they are effective for improving blood flows in the cerebral and coronary arteries and the capillary vessels. Furthermore, the compounds of the present invention have an action of controlling coagulation of blood platelets. Accordingly, they are suitable as agents for remedy of various diseases caused by troubles in blood flows in capillary vessels, cerebral blood vessel disorders and sequelae thereof, stenocardia and cardiac infraction. Moreover, theobromine derivatives provided according to the present invention are excellent in other various pharmacological actions such as the action to the central vervous system, the anti-histaminic action, the amalgesic action, and anti-asthmatic action and the hypotensive action. Accordingly, the compounds of the present invention can effectively be used as psychic energizers, anti-histaminic agents, analgesic agents, anti-asthmatic agents and hypotensive agents.

Compounds [IV] of the present invention can be prepared according to various processes. For example, a process represented by the following reaction formula is ordinarily adopted:

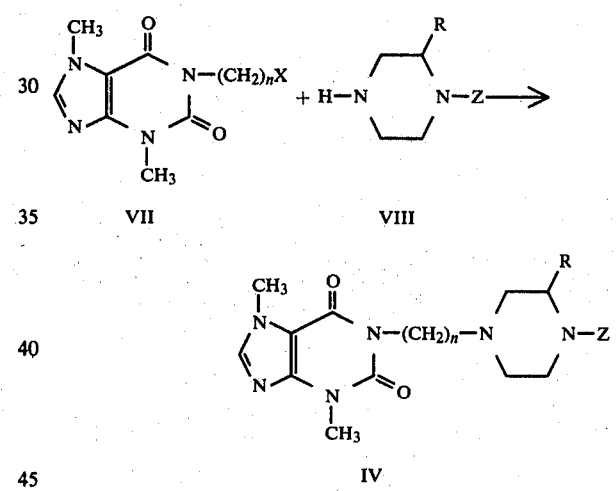

wherein X stands for a halogen atom or a p-toluenesulfonyloxy group, and R, Z and n are as defined above.

In short, a compound IV of the present invention can be obtained by reacting a compound represented by the general formula VII with a compound represented by the general formula VIII.

This reaction is carried out in the absence of a solvent or in the presence of a solvent not participating in the reaction, which is appropriately selected from lower alcohols such as methanol, ethanol, propanol and isopropanol, benzene type solvents such as benzene, toluene and xylene, and ethers such as ethyl ether and tetrahydrofuran. The reaction can be advanced even at room temperature, but it is preferred that the reaction be carried out at an elevated temperature of up to the boiling point of the solvent. The reaction can be performed more smoothly by adding an acid binder such as triethylamine, an alkali metal bicarbonate, an alkali metal carbonate or pyridine to the reaction mixture.

Excellent physiological actions of the theophylline compound according to the invention will now be described with reference to typical compounds.

Blood Flow-Increasing Action

1. Methods

Male and female mongrel dogs having a body weight of 8 to 20 Kg were used as test animals, and the blood flows in the vertebral and femoral arteries were measured. More specifically, probes of an electromagnetic flow meter (Model MF-27 supplied by Nippon Koden) were attached to one side vertebral artery and one side femoral artery of a dog anesthetized by diethyl barbital (240 mg/kg, hypodermic injection) and sodium pentobarbital (10 mg/Kg, intravenous injection), and the blood flows of both the arteries were simultaneously measured. The test compound was administered by artery puncture at a dose of 0.1, 1 or 10 μg per Kg of the body weight.

2. Results

The obtained results are shown in Table 2.

The intensity of the increase of the blood flow referred to in Table 2 was determined by using papaverine as a reference sample. The intensity of the sample having a minimum effective dose of 0.1 microgram/Kg was designated as A and the intensity of the sample having a minimum effective dose of 1.0 microgram/Kg was designated as B. Samples having a minimum effective dose of 10 microgram/Kg were divided into two groups, one having an intensity higher than that of papaverine, and the intensity of the former group was designated as C and the intensity of the latter group was designated as D. The intensity of the sample having no activity was designated as E. Data of the increase of the blood flow and the duration of action, obtained with respect to 10 cases by using paraverine, are shown in Table 1.

TABLE 1

|  | Dose (microgram/kg) | Increase in Blood Flow (mean ± SE) (ml) | Duration of Action (minutes) |
|---|---|---|---|
| Vertebral Artery | 1 | 0.3 ± 0.2 | 0.08 ± 0.05 |
|  | 10 | 11.3 ± 2.7 | 0.55 ± 0.07 |
| Femoral Artery | 1 | 0.4 ± 0.3 | 0.09 ± 0.06 |
|  | 10 | 12.6 ± 2.7 | 0.54 ± 0.07 |

TABLE 2

| Compound |  | Class of Activity | Increase in Blood Flow (ml) | Duration of Action (minutes) | Dose (microgram/kg) |
|---|---|---|---|---|---|
| 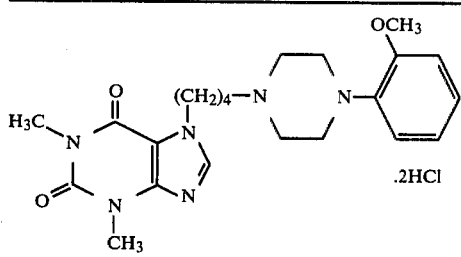 | vertebral artery | A | 101 | 7.8 | 0.1 |
|  | femoral artery | A | 27 | 1.7 | 0.1 |
| 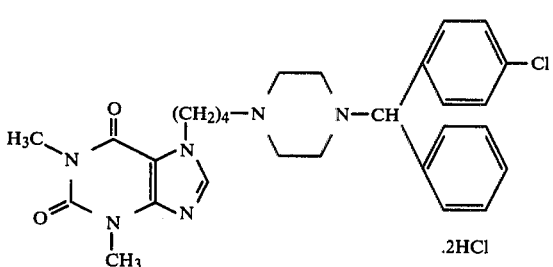 | vertebral artery | D | 2 | 0.7 | 10 |
|  | femoral artery | C | 16 | 0.7 | 10 |
| 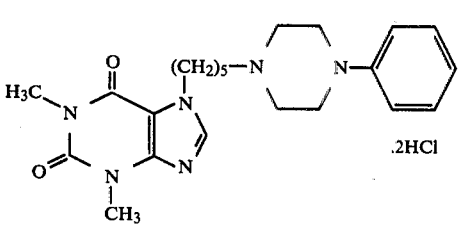 | vertebral artery | A | 4 | 0.6 | 0.1 |
|  | femoral artery | A | 22 | 1.3 | 0.1 |

TABLE 2-continued

| Compound | | Class of Activity | Increase in Blood Flow (ml) | Duration of Action (minutes) | Dose (microgram/kg) |
|---|---|---|---|---|---|
| 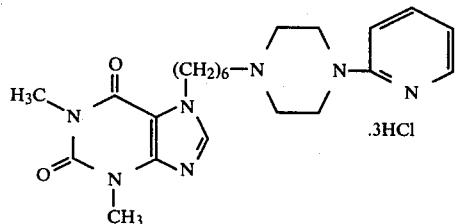 | vertebral artery | B | 4 | 0.5 | 1 |
| | femoral artery | B | 30 | 1.0 | 1 |

The theobromine derivatives were also examined in the same manner as described before in connection with the theophylline derivatives. Results are shown in Tables 3 and 4. From the results shown in Table 4, it will readily be understood that the compounds of the theobromine type have a very excellent blood flow-increasing action.

TABLE 3

| | Dose (microgram/kg) | Increase in Blood Flow (means ± SE) (ml) | Duration of Action (minutes) |
|---|---|---|---|
| Vertebral Artery | 1 | 0.3 ± 0.2 | 0.08 ± 0.05 |
| | 10 | 11.3 ± 2.7 | 0.55 ± 0.07 |
| Femoral Artery | 1 | 0.4 ± 0.3 | 0.09 ± 0.06 |
| | 10 | 12.6 ± 2.7 | 0.54 ± 0.07 |

TABLE 4

| Compound | | Class of Activity | Increase in flood flow (ml) | Duration of Action (minutes) | Dose (microgram/kg) |
|---|---|---|---|---|---|
| 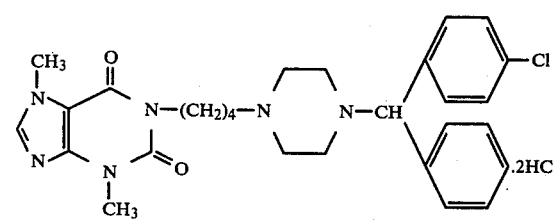 | vertebral artery | C | 65.4 | 1.52 | 10 |
| | femoral artery | C | 94.1 | 1.72 | 10 |
| 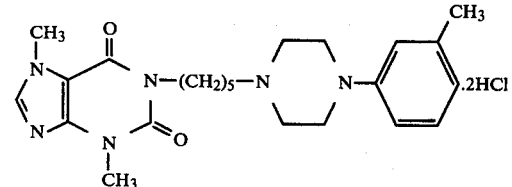 | vertebral artery | A | 18.7 | 0.69 | 0.1 |
| | femoral artery | A | 8.5 | 0.76 | 0.1 |
| 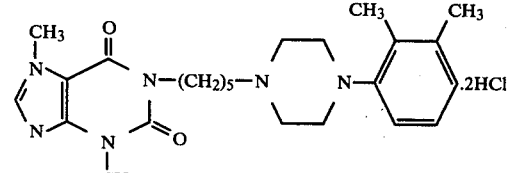 | vertebral artery | B | 27.8 | 0.68 | 1 |
| | femoral artery | B | 84.5 | 1.89 | 1 |
| 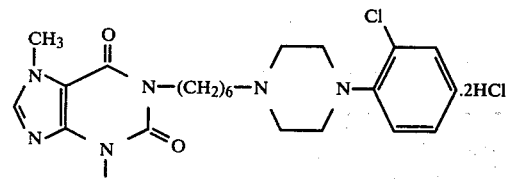 | vertebral artery | A | 15.4 | 1.39 | 0.1 |
| | femoral artery | A | 107.9 | 2.16 | 0.1 |

15

The present invention will now be described in detail with reference to the following Examples that by no means limit the scope of the present invention.

EXAMPLE 1

Synthesis of 7-{2-[4-p-chlorobenzhydrylpiperazinyl-(1)]-ethyl}-theophylline hydrochloride In benzene, 6.3 g of 7-(2-bromoethyl)theophylline, 5.7 g of 1-(p-chlorobenzhydryl)piperazine and 4.0 g of triethylamine are stirred under reflux for 18.5 hours. Triethylamine hydrochloride is removed by filtration and the filtrate is extracted with dilute hydrochloric acid. The extract is made alkaline by dilute sodium hydroxide and is then extracted with chloroform. The chloroform layer is washed with water and dried with anhydrous potassium carbonate. The solvent is removed by distillation and the residual crude crystal is converted to a hydrochloride according to customary procedures. The hydrochloride is recrystallized from methyl cellosolve and water to obtain 4.8 g of intended 7-{2-[4-p-chlorobenzhydrylpiperazinyl-(1)]-ethyl}-theophylline hydrochloride (the yield being 42.5%).

Melting Point: 250°–252° C.

Elementary Analysis Values as $C_{26}H_{29}O_2N_6CH.2HCl$: Calculated: C=55.16%, H=5.53%, N=14.85%, Found: C=55.19%, H=5.38%, N=14.87%.

EXAMPLE 2

Synthesis of 7-{4-[4-o-methoxyphenylpiperazinyl-(1)]-n-butyl}-theophylline

In benzene, 6.9 g of 7-(4-bromo-n-butyl)theophylline, 3.8 g of o-methoxyphenylpiperazine and 4.0 g of triethylamine are stirred under reflux for 18 hours. The subsequent treatments are carried out in the same manner as described in Example 1. The obtained crude crystal is recrystallized from ethanol to obtain 3.8 g of intended 7-{4-[4-o-methoxyphenylpiperazinyl-(1]-n-butyl}-theophylline (the yield being 37.6%).

Melting Point: 117°–118° C.

Elementary Analysis Values as $C_{22}H_{30}O_3N_6$: Calculated: C=61.94%, H=7.10%, N=19.71%, Found: C=62.10%, H=7.21%, N=19.86%.

EXAMPLE 3

Synthesis of 7-{5-[4-o,m-dimethylphenylpiperazinyl-(1)]-n-heptyl}-theophylline

In toluene, 9.9 g of 1-(5-bromo-n-heptyl)theophylline, 3.8 g of o,m-dimethylphenylpiperazine and 4.0 g of triethylamine are stirred under reflux for 11.5 hours, and the subsequent treatments are carried out in the same manner as described in Example 1. The obtained crude crystal is recrystallized from ethanol to obtain 4.3 g of intended 7-{5-[4-o,m-dimethylphenylpiperazinyl-(1)]-n-heptyl}-theophylline.

Melting Point: 115°–117° C.

Elementary Analysis Values as $C_{24}H_{34}O_2N_6$: Calculated: C=65.71%, H=7.38%, N=19.16%, Found: C=65.42%, H=7.92%, N=19.31%.

EXAMPLE 4

Synthesis of 7-{7-[(3-methyl-4-m-methylphenyl)piperazinyl-(1)]-n-heptyl}-theophylline hydrochloride In toluene, 7.8 g of 7-(7-bromo-n-heptyl)theophylline, 3.8 g of N-(m-methylphenyl)-2-methyl-N-piperazine and 4.0 g of triethylamine are stirred under reflux for 11 hours. The subsequent treatments are carried out in the same manner as described in Example 1 to obtain 10 g of a crude crystal. The obtained crude crystal is purified by silica gel chromatography and converted to a hydrochloride according to customary procedures to obtain 5.3 g of intended 7-{7-[3-methyl(4-m-methylphenyl)-piperazinyl-(1)]-n-heptyl}-theophylline hydrochloride.

Melting Point: 222°–265° C.

Elementary Analysis Values as $C_{26}H_{39}O_2N_6Cl\cdot 2.\frac{1}{2}H_2O$: Calculated: C=57.02%, H=7.38%, N=15.35%, Found: C=57.00%, H=7.88%, N=15.20%.

EXAMPLES 5 THROUGH 95

Compounds shown in Table 3 are prepared according to the method described in Example 1.

TABLE 5

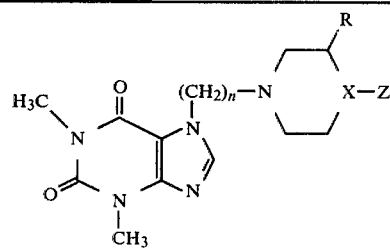

| Example No. | n | X | R | Z | Recrystallization Solvent | Melting Point (°C.) | Molecular Formula | Elementary Analysis Values (upper values: calculated values, lower values: found values) | | |
|---|---|---|---|---|---|---|---|---|---|---|
| | | | | | | | | C (%) | H (%) | N (%) |
| 5 | 2 | N | H | 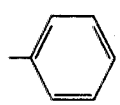 | ethanol | 228–234 (decomposition) | $C_{19}H_{24}O_2N_6.2HCl$ | 51.70 / 51.33 | 9.45 / 9.16 | 19.04 / 18.70 |

TABLE 5-continued

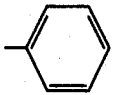

| Example No. | n | X | R | Z | Recrystallization Solvent | Melting Point (°C.) | Molecular Formula | Elementary Analysis Values (upper values: calculated values, lower values: found values) | | |
|---|---|---|---|---|---|---|---|---|---|---|
| | | | | | | | | C (%) | H (%) | N (%) |
| 6 | 3 | N | H | 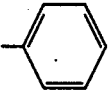 | methanol | 143–145 | $C_{20}H_{26}O_2N_6$ | 62.79<br>62.66 | 6.87<br>6.90 | 21.98<br>22.01 |
| 7 | 4 | N | H | 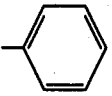 | ethanol | 114–115 | $C_{21}H_{28}O_2N_6$ | 63.60<br>63.61 | 7.13<br>7.25 | 21.20<br>21.34 |
| 8 | 5 | N | H | 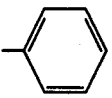 | ethanol/isopropyl ether | 112–113 | $C_{22}H_{30}O_2N_6$ | 64.35<br>64.44 | 7.38<br>7.49 | 20.47<br>20.43 |
| 9 | 6 | N | H | 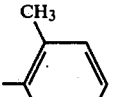 | ethanol/isopropyl ether | 200–203 (decomposition) | $C_{23}H_{32}O_2N_6 \cdot 2HCl$ | 55.52<br>55.26 | 6.90<br>6.71 | 16.90<br>16.59 |
| 10 | 2 | N | H | 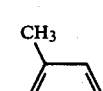 CH₃ | ethanol | 149–150 | $C_{20}H_{26}O_2N_6$ | 62.80<br>62.52 | 6.85<br>6.85 | 21.98<br>21.81 |
| 11 | 3 | N | H | 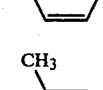 CH₃ | ethanol | 114–116 | $C_{21}H_{28}O_2N_6$ | 63.60<br>63.26 | 7.13<br>7.21 | 21.20<br>20.75 |
| 12 | 5 | N | H | 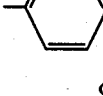 CH₃ | ethanol/isopropyl ether | 113–114 | $C_{22}H_{32}O_2N_6$ | 65.05<br>65.08 | 7.61<br>7.80 | 19.80<br>19.75 |
| 13 | 2 | N | H | CH₃ 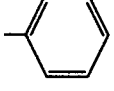 | ethanol | 121–122 | $C_{20}H_{26}O_2N_6$ | 62.80<br>62.98 | 6.85<br>6.83 | 21.98<br>21.97 |
| 14 | 4 | N | H | CH₃ | ethanol | 237–239 (decomposition) | $C_{22}H_{30}O_2N_6 \cdot 2HCl$ | 54.66<br>54.57 | 6.67<br>6.69 | 17.39<br>17.47 |

TABLE 5-continued

Structure:

$$\text{H}_3\text{C-N-C(=O)-[xanthine core with N-CH}_3\text{]-(CH}_2)_n\text{-N[piperazine with R]-X-Z}$$

| Example No. | n | X | R | Z | Recrystallization Solvent | Melting Point (°C.) | Molecular Formula | C (%) | H (%) | N (%) |
|---|---|---|---|---|---|---|---|---|---|---|
| 15 | 5 | N | H | 3-CH$_3$-phenyl | ethanol | 239–241 (decomposition) | C$_{23}$H$_{32}$O$_2$N$_6$.2HCl | 55.30 / 55.32 | 6.87 / 6.90 | 16.83 / 16.98 |
| 16 | 6 | N | H | 3-CH$_3$-phenyl | ethanol | 224–226 (decomposition) | C$_{24}$H$_{34}$O$_2$N$_6$.2HCl | 56.35 / 56.05 | 7.09 / 7.10 | 16.43 / 16.42 |
| 17 | 2 | N | H | 2,4-di-CH$_3$-phenyl | ethanol/isopropyl ether | 103–106 | C$_{21}$H$_{28}$O$_2$N$_6$ | 63.61 / 63.64 | 7.12 / 7.03 | 21.20 / 21.05 |
| 18 | 3 | N | H | 2,4-di-CH$_3$-phenyl | ethanol | 116–118 | C$_{22}$H$_{30}$O$_2$N$_6$ | 64.35 / 64.31 | 7.38 / 7.48 | 20.47 / 20.52 |
| 19 | 4 | N | H | 2,4-di-CH$_3$-phenyl | ethanol | 275–276 (decomposition) | C$_{23}$H$_{32}$N$_6$O$_2$.HCl | 59.92 / 59.54 | 7.21 / 7.26 | 18.23 / 18.05 |
| 20 | 5 | N | H | 2,4-di-CH$_3$-phenyl | ethanol | 136–138 | C$_{24}$H$_{34}$O$_2$N$_6$ | 65.71 / 66.00 | 7.83 / 7.94 | 19.16 / 19.13 |
| 21 | 6 | N | H | 2,4-di-CH$_3$-phenyl | ethanol/isopropyl ether | 167–170 (decomposition) | C$_{25}$H$_{30}$O$_2$N$_6$.2HCl | 57.14 / 56.75 | 7.30 / 7.50 | 15.99 / 16.44 |

TABLE 5-continued

Structure:

$H_3C-N$ ... (xanthine core) ... $(CH_2)_n-N$ (piperazine ring with X-Z) with R substituent

| Example No. | n | X | R | Z | Recrystallization Solvent | Melting Point (°C.) | Molecular Formula | C (%) | H (%) | N (%) |
|---|---|---|---|---|---|---|---|---|---|---|
| 22 | 2 | N | H | 2,6-(CH$_3$)$_2$-C$_6$H$_3$ | ethanol | 151–152 | C$_{21}$H$_{28}$O$_2$N$_6$ | 63.61 / 63.93 | 7.12 / 7.17 | 21.20 / 21.26 |
| 23 | 3 | N | H | 2,6-(CH$_3$)$_2$-C$_6$H$_3$ | ethanol | 153–155 | C$_{22}$H$_{30}$O$_2$N$_6$ | 64.36 / 64.08 | 7.38 / 7.46 | 20.48 / 20.10 |
| 24 | 4 | N | H | 2,6-(CH$_3$)$_2$-C$_6$H$_3$ | ethanol | 114–116 | C$_{23}$H$_{32}$O$_2$N$_6$ | 65.05 / 64.63 | 7.61 / 7.53 | 19.80 / 19.79 |
| 25 | 5 | N | H | 2,6-(CH$_3$)$_2$-C$_6$H$_3$ | ethanol | 115–117 | C$_{24}$H$_{34}$O$_2$N$_6$ | 65.71 / 65.42 | 7.38 / 7.97 | 19.16 / 19.31 |
| 26 | 2 | N | H | 2,4-(CH$_3$)$_2$-C$_6$H$_3$ | ethanol | 140–141 | C$_{21}$H$_{28}$O$_2$N$_6$ | 63.61 / 63.46 | 7.12 / 6.96 | 21.20 / 21.12 |
| 27 | 3 | N | H | 2,4-(CH$_3$)$_2$-C$_6$H$_3$ | ethanol | 128–129 | C$_{22}$H$_{30}$O$_2$N$_6$ | 64.36 / 63.71 | 7.37 / 7.43 | 20.47 / 20.34 |
| 28 | 4 | N | H | 2,4-(CH$_3$)$_2$-C$_6$H$_3$ | ethanol | 251–252 (decomposition) | C$_{23}$H$_{34}$O$_2$N$_6$·HCl | 59.92 / 59.99 | 7.21 / 7.33 | 18.23 / 18.33 |

Elementary Analysis Values (upper values: calculated values, lower values: found values)

TABLE 5-continued

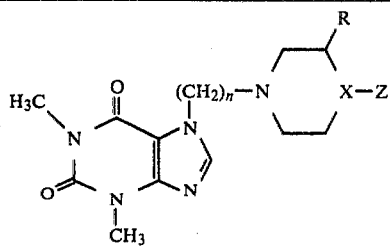

| Example No. | n | X | R | Z | Recrystallization Solvent | Melting Point (°C.) | Molecular Formula | Elementary Analysis Values (upper values: calculated values, lower values: found values) | | |
|---|---|---|---|---|---|---|---|---|---|---|
| | | | | | | | | C (%) | H (%) | N (%) |
| 29 | 5 | N | H | 2,4-(CH$_3$)$_2$-C$_6$H$_3$ | ethanol/ isopropyl ether | 80–83 | C$_{24}$H$_{34}$O$_2$N$_6$·½H$_2$O | 64.39 64.63 | 7.90 7.92 | 18.78 19.26 |
| 30 | 2 | N | H | 2-OCH$_3$-C$_6$H$_4$ | methyl cellosolve | 272–273 (decomposition) | C$_{20}$H$_{20}$O$_3$N$_6$·2HCl | 50.95 50.76 | 6.00 5.68 | 17.83 17.52 |
| 31 | 3 | N | H | 2-OCH$_3$-C$_6$H$_4$ | methanol | 240–243 (decomposition) | C$_{21}$H$_{28}$O$_3$N$_6$·2HCl | 51.95 51.76 | 6.24 6.15 | 17.31 16.98 |
| 32 | 4 | N | H | 2-OCH$_3$-C$_6$H$_4$ | ethanol | 117–118 | C$_{22}$H$_{30}$O$_3$N$_6$ | 61.94 62.10 | 7.10 7.21 | 19.71 19.86 |
| 33 | 5 | N | H | 2-OCH$_3$-C$_6$H$_4$ | ethanol | 120–121 | C$_{23}$H$_{32}$O$_3$N$_6$·H$_2$O | 60.23 60.50 | 7.49 7.20 | 18.33 18.37 |
| 34 | 6 | N | H | 2-OCH$_3$-C$_6$H$_4$ | ethanol/ isopropyl ether | 213–215 (decomposition) | C$_{24}$H$_{34}$O$_3$N$_6$·2HCl | 54.63 54.61 | 6.89 6.58 | 15.93 15.49 |
| 35 | 2 | N | H | 3-OCH$_3$-C$_6$H$_4$ | methyl cellosolve | 170–171 | C$_{20}$H$_{26}$O$_3$N$_6$ | 60.28 60.58 | 6.58 6.63 | 21.09 21.14 |
| 36 | 3 | N | H | 3-OCH$_3$-C$_6$H$_4$ | methyl cellosolve | 161–163 | C$_{21}$H$_{28}$O$_3$N$_6$ | 61.13 61.12 | 6.85 6.85 | 20.38 20.58 |

TABLE 5-continued

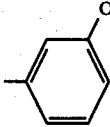

| Example No. | n | X | R | Z | Recrystallization Solvent | Melting Point (°C.) | Molecular Formula | Elementary Analysis Values (upper values: calculated values, lower values: found values) | | |
|---|---|---|---|---|---|---|---|---|---|---|
| | | | | | | | | C (%) | H (%) | N (%) |
| 37 | 4 | N | H | 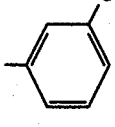 3-OCH$_3$-phenyl | methanol | 211–212 (decomposition) | C$_{22}$H$_{30}$O$_3$N$_6$·HCl | 57.07 / 56.99 | 6.75 / 6.64 | 18.15 / 18.05 |
| 38 | 5 | N | H | 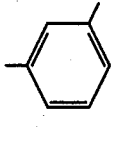 3-OCH$_3$-phenyl | ethanol | 120–121 | C$_{23}$H$_{32}$O$_3$N$_6$·H$_2$O | 60.23 / 60.50 | 7.49 / 7.20 | 18.33 / 18.37 |
| 39 | 6 | N | H | 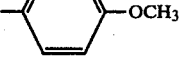 3-OCH$_3$-phenyl | ethanol | 208–210 (decomposition) | C$_{24}$H$_{34}$O$_3$N$_6$·2HCl | 54.64 / 54.51 | 6.88 / 6.91 | 15.93 / 15.99 |
| 40 | 2 | N | H | 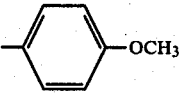 4-OCH$_3$-phenyl | ethanol | 155–156 | C$_{20}$H$_{26}$O$_3$N$_6$ | 60.28 / 60.12 | 6.58 / 6.59 | 21.09 / 21.05 |
| 41 | 3 | N | H | 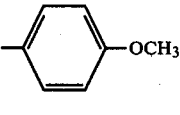 4-OCH$_3$-phenyl | methyl cellosolve | 165–167 | C$_{21}$H$_{28}$O$_3$N$_6$ | 61.13 / 61.18 | 6.85 / 6.92 | 20.38 / 20.26 |
| 42 | 4 | N | H | 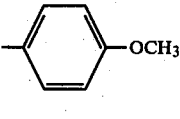 4-OCH$_3$-phenyl | ethanol | 115–116 | C$_{22}$H$_{30}$O$_3$N$_6$ | 61.94 / 61.77 | 7.10 / 7.20 | 19.71 / 19.46 |
| 43 | 5 | N | H | 4-OCH$_3$-phenyl | ethanol | 127–129 | C$_{23}$H$_{32}$O$_3$N$_6$ | 62.69 / 62.36 | 7.33 / 7.33 | 19.08 / 19.41 |
| 44 | 4 | N | H | 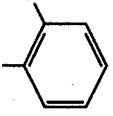 2-Cl-phenyl | ethanol/methyl cellosolve | 161–162 | C$_{19}$H$_{23}$O$_2$N$_6$Cl | 56.64 / 56.79 | 5.77 / 5.60 | 20.86 / 20.93 |
| 45 | 3 | N | H | 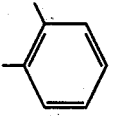 2-Cl-phenyl | ethanol | 121–122 | C$_{20}$H$_{25}$O$_2$N$_6$Cl | 57.61 / 57.64 | 6.06 / 5.96 | 20.16 / 20.23 |

TABLE 5-continued

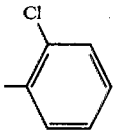

| Example No. | n | X | R | Z | Recrystallization Solvent | Melting Point (°C.) | Molecular Formula | Elementary Analysis Values (upper values: calculated values, lower values: found values) | | |
|---|---|---|---|---|---|---|---|---|---|---|
| | | | | | | | | C (%) | H (%) | N (%) |
| 46 | 2 | N | H | 2-Cl-C$_6$H$_4$ | acetone | 117–119 | C$_{22}$H$_{29}$O$_2$N$_6$Cl | 59.37 59.53 | 6.58 6.80 | 18.89 19.11 |
| 47 | 2 | N | H | 3-Cl-C$_6$H$_4$ | methyl cellosolve | 134–136 | C$_{19}$H$_{23}$O$_2$N$_6$Cl | 56.63 56.86 | 5.77 5.93 | 20.86 20.63 |
| 48 | 3 | N | H | 3-Cl-C$_6$H$_4$ | ethanol | 109–111 | C$_{20}$H$_{25}$O$_2$N$_6$Cl | 57.61 57.55 | 6.06 6.35 | 20.16 19.00 |
| 49 | 4 | N | H | 3-Cl-C$_6$H$_4$ | isopropanol/ isopropyl ether | 96–98 | C$_{21}$H$_{27}$O$_2$N$_6$Cl | 58.52 58.82 | 6.33 6.41 | 19.51 19.26 |
| 50 | 5 | N | H | 3-Cl-C$_6$H$_4$ | ethanol/ methanol | 151–154 | C$_{22}$H$_{31}$O$_2$N$_6$Cl$_3$·½H$_2$O | 50.04 50.02 | 6.13 6.17 | 16.23 15.93 |
| 51 | 2 | N | H | 4-Cl-C$_6$H$_4$ | methyl cellosolve | 167–169 | C$_{19}$H$_{23}$O$_2$N$_6$Cl | 56.63 56.66 | 5.77 5.81 | 20.86 20.91 |
| 52 | 3 | N | H | 4-Cl-C$_6$H$_4$ | methyl cellosolve | 241–244 (decomposition) | C$_{20}$H$_{25}$O$_2$N$_6$Cl·2HCl | 49.03 48.66 | 5.57 5.20 | 17.16 16.84 |
| 53 | 4 | N | H | 4-Cl-C$_6$H$_4$ | ethanol | 107–109 | C$_{21}$H$_{27}$O$_2$N$_6$Cl | 58.52 58.77 | 6.33 6.38 | 19.50 19.44 |
| 54 | 5 | N | H | 4-Cl-C$_6$H$_4$ | isopropanol/ ether | 127–130 | C$_{22}$H$_{29}$O$_2$N$_6$Cl·2HCl | 51.01 50.49 | 6.05 6.20 | 16.23 16.02 |

TABLE 5-continued

[Structure: 1,3-dimethylxanthine with 7-position substituent $(CH_2)_n-N$(piperazine ring with R substituent)$-X-Z$]

| Example No. | n | X | R | Z | Recrystallization Solvent | Melting Point (°C.) | Molecular Formula | C (%) | H (%) | N (%) |
|---|---|---|---|---|---|---|---|---|---|---|
| 55 | 6 | N | H | 4-Cl-phenyl | methanol | 110–111 | $C_{23}H_{31}O_2N_6Cl$ | 60.17 / 60.20 | 6.82 / 6.96 | 18.31 / 18.68 |
| 56 | 2 | N | H | 3,4-diCl-phenyl | methyl cellosolve | 146–147 | $C_{19}H_{22}O_2N_6Cl_2$ | 52.18 / 52.23 | 5.07 / 4.95 | 19.22 / 19.39 |
| 57 | 3 | N | H | 3,4-diCl-phenyl | methyl cellosolve | 124–126 | $C_{20}H_{24}O_2N_6Cl_2$ | 53.21 / 53.50 | 5.37 / 5.32 | 18.62 / 18.52 |
| 58 | 4 | N | H | 3,4-diCl-phenyl | methanol | 130–132 | $C_{21}H_{26}O_2N_6Cl_2$ | 54.19 / 54.44 | 5.64 / 5.73 | 18.06 / 18.21 |
| 59 | 3 | N | H | 4-F-phenyl | methanol | 128–129 | $C_{20}H_{25}O_2N_6F$ | 59.97 / 59.94 | 6.30 / 6.31 | 20.99 / 21.12 |
| 60 | 4 | N | H | 4-F-phenyl | methanol | 223–226 (decomposition) | $C_{21}H_{27}O_2N_6F \cdot 2HCl$ | 51.74 / 51.65 | 6.00 / 5.84 | 17.25 / 16.94 |
| 61 | 5 | N | H | 4-F-phenyl | ethanol/methanol | 140–141 | $C_{22}H_{29}O_2N_6F$ | 61.65 / 61.32 | 6.83 / 6.77 | 19.61 / 19.67 |
| 62 | 3 | N | H | 3-CF$_3$-phenyl | methanol | 115–116 | $C_{21}H_{25}O_2N_6F_3$ | 55.98 / 56.46 | 5.60 / 5.71 | 18.66 / 19.26 |
| 63 | 4 | N | H | 3-CF$_3$-phenyl | ethanol/isopropyl ether | 215–218 | $C_{22}H_{26}O_2N_6F_3 \cdot 2HCl$ | 49.16 / 49.25 | 5.26 / 5.42 | 15.64 / 16.21 |

Elementary Analysis Values (upper values: calculated values, lower values: found values)

TABLE 5-continued

Structure:

$H_3C$-N(1), N(3)-$CH_3$ dimethylxanthine with $(CH_2)_n$-N-piperazine (X-Z) with R substituent

| Example No. | n | X | R | Z | Recrystallization Solvent | Melting Point (°C.) | Molecular Formula | Elementary Analysis Values (upper: calculated, lower: found) | | |
|---|---|---|---|---|---|---|---|---|---|---|
| | | | | | | | | C (%) | H (%) | N (%) |
| 64 | 5 | N | H | 3-CF$_3$-phenyl | ethanol/isopropyl ether | 114–115 | $C_{23}H_{29}O_2N_6F_3$ | 57.72<br>57.55 | 6.12<br>6.13 | 17.56<br>17.71 |
| 65 | 2 | N | H | 2-pyridyl | methanol | 153–155 | $C_{18}H_{23}O_2N_7$ | 58.51<br>58.48 | 6.29<br>6.38 | 26.54<br>26.22 |
| 66 | 3 | N | H | 2-pyridyl | ethanol | 139–140 | $C_{19}H_{25}O_2N_7$ | 59.50<br>59.52 | 6.58<br>6.65 | 25.57<br>25.80 |
| 67 | 4 | N | H | 2-pyridyl | ethanol | 120–121 | $C_{20}H_{27}O_2N_7$ | 60.42<br>60.14 | 6.86<br>6.90 | 24.67<br>24.40 |
| 68 | 5 | N | H | 2-pyridyl | ethanol/isopropyl ether | 102–104 | $C_{21}H_{29}O_2N_7$ | 61.28<br>61.26 | 7.12<br>7.11 | 23.83<br>23.66 |
| 69 | 6 | N | H | 2-pyridyl | ethanol | 96–97 | $C_{22}H_{31}O_2N_7$ | 62.08<br>62.01 | 7.36<br>7.46 | 23.04<br>23.35 |
| 70 | 3 | N | H | -CH(phenyl)$_2$ | methyl cellosolve | 252–254 | $C_{27}H_{32}O_2N_6 \cdot 2HCl$ | 59.44<br>59.28 | 6.29<br>6.42 | 15.41<br>15.59 |
| 71 | 4 | N | H | -CH(phenyl)$_2$ | ethanol/methanol | 238–240 | $C_{28}H_{34}O_2N_6 \cdot 2HCl$ | 60.09<br>59.14 | 6.50<br>6.48 | 15.02<br>14.93 |

TABLE 5-continued

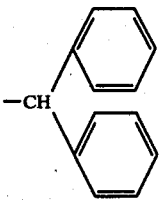

| Example No. | n | X | R | Z | Recrystallization Solvent | Melting Point (°C.) | Molecular Formula | Elementary Analysis Values (upper values: calculated values, lower values: found values) | | |
|---|---|---|---|---|---|---|---|---|---|---|
| | | | | | | | | C (%) | H (%) | N (%) |
| 72 | 5 | N | H | —CH(C₆H₅)₂ | methyl cellosolve | 115–117 (decomposition) | C₂₉H₃₆O₂N₆ | 69.56 69.87 | 7.26 7.39 | 16.79 16.70 |
| 73 | 6 | N | H | —CH(C₆H₅)₂ | ethanol | 212–214 | C₃₀H₃₈O₂N₆·2HCl | 61.30 61.27 | 6.87 7.04 | 14.30 14.51 |
| 74 | 2 | N | H | —CH(C₆H₄Cl)(C₆H₅) | methyl cellosolve | 250–252 | C₂₆H₂₉O₂N₆Cl·2HCl | 55.16 55.19 | 5.53 5.38 | 14.85 14.87 |
| 75 | 3 | N | H | —CH(C₆H₄Cl)(C₆H₅) | methyl cellosolve | 222 (decomposition) | C₂₇H₃₁O₂N₆Cl·2HCl·H₂O | 54.22 53.64 | 5.91 5.92 | 14.06 14.09 |
| 76 | 4 | N | H | —CH(C₆H₄Cl)(C₆H₅) | methanol | 208–210 | C₂₈H₃₃O₂N₆Cl·2HCl | 56.61 55.97 | 5.95 6.04 | 14.15 13.92 |

TABLE 5-continued

[Structure: 1,3-dimethylxanthine-imidazole core with (CH$_2$)$_n$-N-piperazine/piperidine X-Z substituent with R group]

| Example No. | n | X | R | Z | Recrystallization Solvent | Melting Point (°C.) | Molecular Formula | C (%) | H (%) | N (%) |
|---|---|---|---|---|---|---|---|---|---|---|
| 77 | 5 | N | H | —CH(C$_6$H$_5$)(4-Cl-C$_6$H$_4$) | ethanol/isopropyl ether | 117–119 | C$_{29}$H$_{35}$O$_2$N$_6$Cl | 65.08 / 65.23 | 6.60 / 6.64 | 15.70 / 16.02 |
| 78 | 6 | N | H | —CH(C$_6$H$_5$)(4-Cl-C$_6$H$_4$) | ethanol | 201–203 | C$_{30}$H$_{37}$O$_2$N$_6$Cl·2HCl·½H$_2$O | 57.09 / 57.00 | 6.40 / 6.54 | 13.32 / 13.90 |
| 79 | 2 | N | —CH$_3$ | C$_6$H$_5$ | ethanol | 128–130 | C$_{20}$H$_{26}$O$_2$N$_6$ | 62.80 / 62.73 | 6.85 / 6.87 | 21.98 / 21.91 |
| 80 | 4 | N | —CH$_3$ | C$_6$H$_5$ | isopropanol | 99–100 | C$_{22}$H$_{30}$O$_2$N$_6$ | 64.36 / 64.51 | 7.37 / 7.47 | 20.47 / 20.87 |
| 81 | 5 | N | —CH$_3$ | C$_6$H$_5$ | acetone/isopropyl ether | 111–113 | C$_{21}$H$_{28}$O$_2$N$_6$ | 63.28 / 63.74 | 7.09 / 7.12 | 21.09 / 21.35 |
| 82 | 2 | N | —CH$_3$ | 4-OCH$_3$-C$_6$H$_4$ | ethanol | 117–118 | C$_{21}$H$_{28}$N$_6$O$_3$ | 61.14 / 61.00 | 6.84 / 6.94 | 20.38 / 20.23 |
| 83 | 5 | N | —CH$_3$ | 4-OCH$_3$-C$_6$H$_4$ | isopropanol | 85–87 | C$_{24}$H$_{31}$O$_3$N$_6$ | 63.82 / 63.56 | 6.93 / 7.69 | 18.61 / 18.63 |
| 84 | 2 | C | H | C$_6$H$_5$ | methanol | 155–156 | C$_{20}$H$_{25}$O$_2$N$_5$ | 65.36 / 65.69 | 6.87 / 6.80 | 19.06 / 19.17 |

TABLE 5-continued

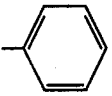

| Example No. | n | X | R | Z | Recrystallization Solvent | Melting Point (°C.) | Molecular Formula | C (%) | H (%) | N (%) |
|---|---|---|---|---|---|---|---|---|---|---|
| 85 | 3 | C | H | 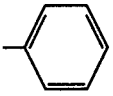 | methyl cellosolve | 157–159 | $C_{21}H_{27}O_2N_5$ | 66.10 / 66.05 | 7.15 / 7.16 | 18.36 / 18.55 |
| 86 | 4 | C | H | 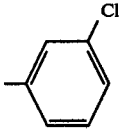 | ethanol | 117–118 | $C_{22}H_{29}O_2N_5$ | 66.80 / 67.01 | 7.40 / 7.51 | 17.71 / 17.70 |
| 87 | 7 | N | —CH₃ | 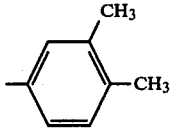 Cl | ethanol/ isopropyl ether | 200–204 | $C_{25}H_{35}O_2N_6Cl \cdot HCl \cdot H_2O$ | 55.44 / 55.36 | 7.09 / 6.88 | 15.52 / 15.92 |
| 88 | 7 | N | H | 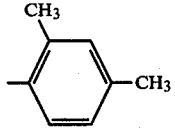 CH₃, CH₃ | hydrous ethanol | 239–241 | $C_{26}H_{37}O_2N_6 \cdot 2HCl \cdot \frac{1}{2}H_2O$ | 57.02 / 57.46 | 7.38 / 7.45 | 15.35 / 15.77 |
| 89 | 8 | N | H | 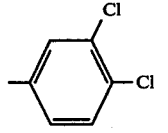 CH₃, CH₃ | hydrous ethanol | 181–183 | $C_{27}H_{40}N_6O_2 \cdot 2HCl$ | 58.79 / 58.71 | 7.68 / 7.58 | 15.24 / 15.22 |
| 90 | 5 | N | H | 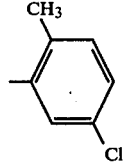 Cl, Cl | ethanol/ isopropyl ether | 112–114 | $C_{22}H_{26}O_2N_6 \cdot 2HCl$ | 55.11 / 55.09 | 5.90 / 5.93 | 17.53 / 17.31 |
| 91 | 7 | N | H | 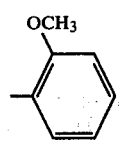 CH₃, Cl | hydrous methanol | 223–226 (decomposition) | $C_{25}H_{35}O_2N_6Cl \cdot 2HCl$ | 53.90 / 53.49 | 6.17 / 6.60 | 15.09 / 15.50 |
| 92 | 10 | N | H | OCH₃ | ethanol | 207–209 (decomposition) | $C_{28}H_{41}O_3N_6 \cdot 2HCl$ | 57.71 / 57.76 | 7.45 / 7.91 | 14.43 / 14.11 |

TABLE 5-continued

[Structure: theobromine derivative with R group, (CH₂)ₙ-N-piperazine-X-Z substituent]

| Example No. | n | X | R | Z | Recrystallization Solvent | Melting Point (°C.) | Molecular Formula | C (%) | H (%) | N (%) |
|---|---|---|---|---|---|---|---|---|---|---|
| 93 | 10 | N | H | 4-Cl-phenyl (via CH₃) | ethanol | 211–213 (decomposition) | C₂₈H₄₁O₂N₆Cl.HCl | 59.45 / 59.31 | 7.50 / 7.50 | 14.80 / 14.69 |
| 94 | 10 | N | —CH₃ | 3-CH₃-phenyl | methanol/isopropyl ether | 211–214 (decomposition) | C₂₉H₄₆O₂N₆.2HCl.2H₂O | 56.38 / 56.12 | 8.17 / 7.76 | 13.60 / 13.46 |
| 95 | 10 | N | H | 2,4-di-CH₃-phenyl | methanol/isopropyl ether | 187–190 (decomposition) | C₂₉H₄₄O₂N₆.2HCl | 59.87 / 59.42 | 7.99 / 7.96 | 14.45 / 14.09 |

Elementary Analysis Values (upper values: calculated values, lower values: found values)

EXAMPLE 96

Synthesis of 1-{4-[4-o,m-dimethylphenylpiperazinyl-(1)]-n-butyl}-theobromine

In toluene, 9.5 g of 1-(4-bromo-n-butyl)theobromine, 3.8 g of o,m-dimethylphenylpiperazine and 4.0 g of triethylamine are stirred under reflux for 13 hours. Triethylamine hydrochloride is removed by filtration and the filtrate is extracted with dilute hydrochloric acid. The extract is made alkaline by dilute sodium hydroxide and is then extracted with chloroform. The chloroform layer is washed with water and dried with anhydrous potassium carbonate. The solvent is removed by distillation and the residual crude crystal is recrystallized from methyl cellosolve to obtain 3.7 g of intended 1-{4-[4-o,m-dimethylphenylpiperazinyl-(1)]-n-butyl}-theobromine (the yield being 43.64%).

Melting Point: 134°–135° C.

Elementary Analysis Values as C₂₃H₃₂O₂N₆: Calculated: C=65.05%, H=7.61%, N=19.80%, Found: C=65.11%, H=7.72%, N=19.46%.

EXAMPLE 97

Synthesis of 1-{5-[4-benzhydrylpiperazinyl-(1)]-n-pentyl}-theobromine hydrochloride In toluene, 7.9 g of 1-(5-bromo-n-pentyl)theobromine, 5.0 g of N-benzhydrylpiperazine and 4 g of triethylamine are stirred under reflux for 30 hours. The subsequent treatments are carried out in the same manner as described in Example 96. The obtained crude crystal is converted to a hydrochloride according to customary procedures to obtain 4.7 g of intended 1-{5-[4-benzhydrylpiperazinyl-(1)]-n-pentyl}-theobromine hydrochloride (the yield being 40.9%).

Melting Point: 262°–264° C. (decomposition).

Elementary Analysis Values as C₂₉H₃₆O₂N₆.2HCl: Calculated: C=60.93%, H=6.71%, N=14.71%, Found: C=60.57%, H=7.15%, N=14.65%.

EXAMPLE 98

Synthesis of 1-{7-[4-o-methoxyphenylpiperazinyl-(1)]-n-heptyl}-theobromine

In toluene, 7.5 g of 1-(7-bromo-n-heptyl)theobromine, 3.8 g of N-o-methoxyphenylpiperazine and 4.0 g of triethylamine are stirred under reflux for 11.5 hours, and the subsequent treatments are carried out in the same manner as described in Example 96. The obtained crude crystal is purified by silica gel chromatography to obtain 4.6 g of intended 1- 7-[4-o-methoxyphenylpiperazinyl-(1)]-n-heptyl -theobromine (the yield being 49.1%).

Melting Point: 97°–98° C.

Elementary Analysis Values as C₂₅H₃₆O₃N₆: Calculated: C=64.08%, H=7.74%, N=17.94%, Found: C=63.90%, H=7.67%, N=18.01%.

EXAMPLES 99 THROUGH 148

Compounds shown in Table 6 are prepared according to the method described in Example 96.

TABLE 6

| Example No. | n | R | Z | Recrystallization Solvent | Melting Point (°C.) | Molecular Formula | C (%) | H (%) | N (%) |
|---|---|---|---|---|---|---|---|---|---|
| 99 | 6 | H | 2-CH₃-C₆H₄ | ethanol | 197–198 (decomposition) | $C_{24}H_{34}N_6O_2 \cdot 2HCl \cdot 2H_2O$ | 52.65 / 52.64 | 7.01 / 7.10 | 15.35 / 15.28 |
| 100 | 2 | H | 3-CH₃-C₆H₄ | ethanol | 251 (decomposition) | $C_{20}H_{26}O_2N_6 \cdot 2HCl$ | 52.75 / 52.41 | 6.21 / 6.11 | 18.46 / 18.31 |
| 101 | 5 | H | 3-CH₃-C₆H₄ | ethanol | 133–135 | $C_{23}H_{32}O_2N_6$ | 65.05 / 65.03 | 7.61 / 7.62 | 19.80 / 19.82 |
| 102 | 6 | H | 3-CH₃-C₆H₄ | ethanol | 206–208 (decomposition) | $C_{24}H_{34}O_2N_6 \cdot 2HCl \cdot 2H_2O$ | 52.65 / 53.10 | 7.01 / 6.91 | 15.35 / 15.44 |
| 103 | 2 | H | 2,6-(CH₃)₂-C₆H₃ | ethanol | 151–153 | $C_{21}H_{28}O_2N_6$ | 63.60 / 63.60 | 7.13 / 7.05 | 21.20 / 21.28 |
| 104 | 3 | H | 2,6-(CH₃)₂-C₆H₃ | ethanol | 154–156 | $C_{22}H_{30}O_2N_6$ | 64.36 / 64.13 | 7.37 / 7.49 | 20.47 / 20.32 |
| 105 | 4 | H | 2,6-(CH₃)₂-C₆H₃ | ethanol | 124–126 | $C_{23}H_{32}O_2N_6$ | 65.05 / 65.03 | 7.61 / 7.61 | 19.80 / 19.82 |
| 106 | 5 | H | 2,6-(CH₃)₂-C₆H₃ | ethanol | 121–123 | $C_{24}H_{34}O_2N_6$ | 65.71 / 65.68 | 7.38 / 7.73 | 19.16 / 19.36 |
| 107 | 2 | H | 2,3-(CH₃)₂-C₆H₃ | ethanol | 161–162 | $C_{21}H_{28}O_2N_6$ | 63.60 / 63.67 | 7.13 / 7.07 | 21.20 / 21.16 |
| 108 | 3 | H | 2,3-(CH₃)₂-C₆H₃ | ethanol | 124–126 | $C_{23}H_{30}O_2N_6$ | 64.36 / 63.65 | 7.37 / 7.20 | 20.47 / 20.32 |

(Elementary Analysis Values: upper values: calculated values, lower values: found values)

TABLE 6-continued

[Structure: 1,3-dimethylxanthine-like core with —C(O)—N—(CH₂)ₙ—N(piperazine with R substituent)—N—Z]

| Example No. | n | R | Z | Recrystallization Solvent | Melting Point (°C.) | Molecular Formula | C (%) | H (%) | N (%) |
|---|---|---|---|---|---|---|---|---|---|
| 109 | 4 | H | 2,6-(CH₃)₂-phenyl | methyl cellosolve | 134–135 | $C_{23}H_{32}O_2N_6$ | 65.05 / 65.11 | 7.61 / 7.72 | 19.80 / 19.46 |
| 110 | 5 | H | 2,6-(CH₃)₂-phenyl | ethanol/ isopropyl ether | 118–120 | $C_{24}H_{34}O_2N_6$ | 65.71 / 65.65 | 7.38 / 7.95 | 19.16 / 18.94 |
| 111 | 6 | H | 2,6-(CH₃)₂-phenyl | isopropanol/ isopropyl ether | 91–93 | $C_{25}H_{36}O_2N_6$ | 66.34 / 65.84 | 8.02 / 8.31 | 18.57 / 18.50 |
| 112 | 2 | H | 2,5-(CH₃)₂-phenyl | ethanol | 139–141 | $C_{21}H_{28}O_2N_6$ | 63.61 / 63.73 | 7.12 / 7.30 | 21.20 / 21.21 |
| 113 | 3 | H | 2,5-(CH₃)₂-phenyl | ethanol | 137–139 | $C_{22}H_{30}O_2N_6$ | 64.36 / 64.19 | 7.37 / 7.44 | 20.47 / 20.36 |
| 114 | 4 | H | 2,5-(CH₃)₂-phenyl | ethanol | 148–150 | $C_{23}H_{32}O_2N_6$ | 65.05 / 64.44 | 7.61 / 7.52 | 19.80 / 19.70 |
| 115 | 5 | H | 2,5-(CH₃)₂-phenyl | isopropanol | 99–101 | $C_{24}H_{34}O_2N_6$ | 65.71 / 65.33 | 7.38 / 7.79 | 19.16 / 19.12 |
| 116 | 6 | H | 2,5-(CH₃)₂-phenyl | ethanol/ isopropyl ether | 89–90 | $C_{25}H_{36}O_2N_6$ | 66.33 / 66.26 | 8.03 / 8.21 | 18.57 / 18.24 |
| 117 | 5 | H | 2-OCH₃-phenyl | ethanol | 165–166 (decomposition) | $C_{23}H_{32}O_3N_6 \cdot HCl$ | 57.91 / 57.81 | 6.97 / 7.19 | 17.62 / 17.21 |
| 118 | 6 | H | 2-OCH₃-phenyl | ethanol/ methanol | 79–81 | $C_{24}H_{34}O_3N_6$ | 63.40 / 63.35 | 7.55 / 7.70 | 18.49 / 18.69 |

TABLE 6-continued

[Structure: 1,3-dimethylxanthine-like core with —C(O)—N—(CH$_2$)$_n$—N(piperazine)—N—Z, with R substituent]

| Example No. | n | R | Z | Recrystal- lization Solvent | Melting Point (°C.) | Molecular Formula | C (%) | H (%) | N (%) |
|---|---|---|---|---|---|---|---|---|---|
| 119 | 2 | H | 2-Cl-C$_6$H$_4$ | ethanol | 122–124 | C$_{19}$H$_{23}$O$_2$N$_6$Cl | 56.63 / 56.67 | 5.77 / 5.67 | 20.86 / 21.19 |
| 120 | 4 | H | 2-Cl-C$_6$H$_4$ | isopropanol/ isopropyl ether | 111–113 | C$_{21}$H$_{27}$O$_2$N$_6$Cl · ½H$_2$O | 57.33 / 57.53 | 6.65 / 6.29 | 19.10 / 19.14 |
| 121 | 6 | H | 3-Cl-C$_6$H$_4$ | isopropanol/ methanol | 106–107 | C$_{23}$H$_{31}$O$_2$N$_6$Cl | 60.17 / 60.21 | 6.82 / 6.97 | 18.31 / 18.63 |
| 122 | 2 | —CH$_3$ | C$_6$H$_5$ | methyl cellosolve | 176–178 | C$_{20}$H$_{26}$O$_2$N$_6$ | 62.79 / 63.19 | 6.87 / 6.89 | 21.98 / 22.03 |
| 123 | 3 | —CH$_3$ | C$_6$H$_5$ | ethanol | 126–128 | C$_{21}$H$_{28}$O$_2$N$_6$ | 63.61 / 63.56 | 7.12 / 7.28 | 21.20 / 21.54 |
| 124 | 4 | —CH$_3$ | C$_6$H$_5$ | ethanol | 120–122 | C$_{22}$H$_{30}$O$_2$N$_6$ | 64.35 / 64.81 | 7.38 / 7.47 | 20.47 / 20.37 |
| 125 | 5 | —CH$_3$ | C$_6$H$_5$ | ethanol/ isopropyl ether | 102–104 | C$_{23}$H$_{32}$O$_2$N$_6$ | 65.07 / 65.10 | 7.60 / 7.77 | 19.80 / 19.82 |
| 126 | 6 | —CH$_3$ | C$_6$H$_5$ | ethanol | 101–103 | C$_{24}$H$_{34}$O$_2$N$_6$ | 65.71 / 65.64 | 7.38 / 7.95 | 19.16 / 19.19 |
| 127 | 2 | —CH$_3$ | 4-OCH$_3$-C$_6$H$_4$ | isopropanol | 118–119 | C$_{21}$H$_{28}$O$_3$N$_6$ · ½H$_2$O | 60.27 / 60.73 | 6.28 / 6.81 | 20.09 / 20.15 |
| 128 | 3 | —CH$_3$ | 4-OCH$_3$-C$_6$H$_4$ | methanol | 142–143 | C$_{22}$H$_{30}$O$_3$N$_6$ | 61.95 / 61.95 | 7.09 / 7.13 | 19.71 / 19.91 |
| 129 | 4 | —CH$_3$ | 4-OCH$_3$-C$_6$H$_4$ | ethanol | 108–110 | C$_{23}$H$_{32}$O$_3$N$_6$ | 62.70 / 62.84 | 7.32 / 7.39 | 19.08 / 19.24 |
| 130 | 3 | H | 2,4-Cl$_2$-C$_6$H$_3$ | methyl cellosolve | 162–163 | C$_{20}$H$_{24}$O$_2$N$_6$Cl$_2$ | 53.21 / 53.11 | 5.37 / 5.41 | 18.62 / 18.62 |
| 131 | 4 | H | 2,4-Cl$_2$-C$_6$H$_3$ | methyl cellosolve | 140–142 | C$_{21}$H$_{26}$O$_2$N$_6$Cl$_2$ | 54.19 / 54.24 | 5.64 / 5.71 | 18.06 / 17.91 |
| 132 | 5 | H | 2,4-Cl$_2$-C$_6$H$_3$ | methyl cellosolve | 132–134 | C$_{22}$H$_{28}$O$_2$N$_6$Cl$_2$ | 55.11 / 55.03 | 5.90 / 5.86 | 17.53 / 17.65 |

TABLE 6-continued

[Structure: 1,3-dimethylxanthine-like core with substituent —N—(CH₂)ₙ—N(piperazine with R)N—Z]

| Example No. | n | R | Z | Recrystallization Solvent | Melting Point (°C.) | Molecular Formula | C (%) | H (%) | N (%) |
|---|---|---|---|---|---|---|---|---|---|
| 133 | 6 | H | 3,4-dichlorophenyl | ethanol | 144–145 | $C_{23}H_{30}O_2N_6Cl_2$ | 55.57 / 56.04 | 6.14 / 6.32 | 17.03 / 17.09 |
| 134 | 2 | H | —CH(C₆H₅)₂ | ethanol | 175–176 | $C_{26}H_{30}O_2N$ | 68.10 / 68.20 | 6.59 / 6.57 | 18.33 / 18.50 |
| 135 | 3 | H | —CH(C₆H₅)₂ | ethanol | 150–151 | $C_{27}H_{32}O_2N_6$ | 68.62 / 68.66 | 6.83 / 6.87 | 17.79 / 17.85 |
| 136 | 4 | H | —CH(C₆H₅)₂ | methyl cellosolve | 163–165 | $C_{28}H_{34}O_2N_6$ | 69.10 / 68.96 | 7.06 / 7.00 | 17.27 / 17.22 |
| 137 | 5 | H | —CH(C₆H₅)₂ | isopropanol | 262–264 | $C_{29}H_{36}O_2N_6 \cdot 2HCl$ | 60.93 / 60.57 | 6.71 / 7.15 | 14.71 / 14.65 |
| 138 | 2 | H | —CH(4-Cl-C₆H₄)(C₆H₅) | methanol | 228–230 (decomposition) | $C_{26}H_{29}O_2N_6 \cdot 2HCl \cdot H_2O$ | 53.48 / 54.05 | 5.70 / 5.45 | 14.40 / 14.35 |
| 139 | 3 | H | —CH(4-Cl-C₆H₄)(C₆H₅) | methyl cellosolve | 194–195 (decomposition) | $C_{27}H_{31}O_2N_6 \cdot 2HCl \cdot 2H_2O$ | 52.64 / 53.21 | 5.74 / 5.95 | 13.64 / 13.74 |
| 140 | 4 | H | —CH(4-Cl-C₆H₄)(C₆H₅) | ethanol/isopropyl ether | 142–144 | $C_{28}H_{33}O_2N_6Cl$ | 64.53 / 64.76 | 6.40 / 6.52 | 16.13 / 16.16 |
| 141 | 5 | H | —CH(4-Cl-C₆H₄)(C₆H₅) | methanol/ethanol | 85–87 | $C_{29}H_{35}O_2N_6Cl \cdot 2HCl$ | 57.47 / 56.96 | 6.17 / 6.68 | 13.87 / 13.73 |

TABLE 6-continued

[Structure shown: 1,3-dimethylxanthine-like core with N—(CH₂)ₙ—N-piperazine-N—Z, with R substituent]

| Example No. | n | R | Z | Recrystallization Solvent | Melting Point (°C.) | Molecular Formula | C (%) | H (%) | N (%) |
|---|---|---|---|---|---|---|---|---|---|
| 142 | 6 | H | —CH(C₆H₄Cl)(C₆H₅) | ethanol/isopropyl ether | 85–88 | C₃₀H₃₇O₂N₆Cl .2HCl | 57.92 / 57.56 | 6.33 / 6.69 | 13.51 / 13.14 |
| 143 | 7 | H | C₆H₄—F | acetone/isopropyl ether | 81–83 | C₂₄H₃₃O₂N₆F | 63.12 / 62.69 | 7.30 / 7.33 | 18.41 / 18.33 |
| 144 | 7 | H | C₆H₄—CH₃ | purified by column chromatography (silica gel) | 90–91 | C₂₅H₃₆O₂N₆ | 66.34 / 66.24 | 8.02 / 8.03 | 18.57 / 18.54 |
| 145 | 8 | H | C₆H₄—OCH₃ | hydrous ethanol | 173–177 | C₂₆H₃₈N₆O₃ | 54.44 / 54.19 | 7.38 / 7.37 | 14.65 / 14.67 |
| 146 | 8 | H | C₆H₃(CH₃)₂ | hydrous ethanol | 228–230 | C₂₇H₄₀N₆O₂ .HCl | 62.95 / 62.91 | 8.62 / 8.04 | 16.32 / 16.41 |
| 147 | 10 | H | —C₆H₃(CH₂)(CH₃) | hydrous ethanol | 147–150 | C₂₉H₄₄N₆O₂ .2HCl.H₂O | 58.08 / 58.28 | 8.07 / 8.08 | 14.02 / 13.94 |
| 148 | 10 | —CH₃ | C₆H₄—OCH₃ | ethanol | 154–157 | C₂₉H₄₄N₆O₃ .2HCl.½H₂O | 57.44 / 57.32 | 7.81 / 7.92 | 13.86 / 13.84 |

What is claimed is:

1. A compound having the formula

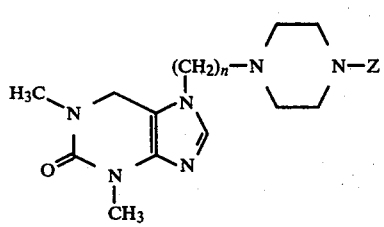

wherein Z is selected from the group consisting of (a) pyridyl and (b)

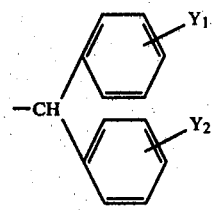

in which $Y_1$ and $Y_2$, which are the same or different, are hydrogen, lower alkyl, lower alkoxy, trifluoromethyl or halogen; and n is an integer of from 2 to 10; or a pharmaceutically acceptable salt thereof.

2. A compound as claimed in claim 1 in which Z is pyridyl.

3. A compound as claimed in claim 1 in which Z is

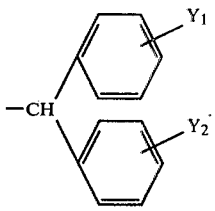

4. A compound as claimed in claim 2 in which n is 3.

5. A compound having the formula

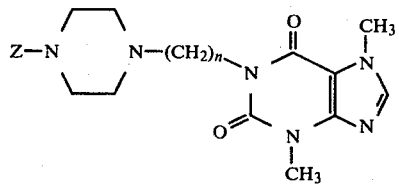

wherein Z is

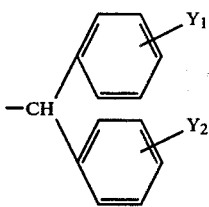

in which $Y_1$ and $Y_2$, which are the same or different, are hydrogen, lower alkyl, lower alkoxy, trifluoromethyl or halogen; and n is an integer of from 2 to 10; or a pharamceutically acceptable salt thereof.

6. A compound as claimed in claim 5 in which n is 5 and Z is benzhydryl.

7. A compound as claimed in claim 5 in which n is 6 and Z is

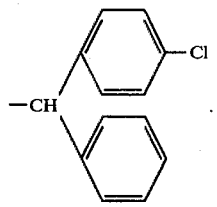

8. A pharmaceutical composition which comprises a therapeutically effective amount of a compound as defined in claim 1, for vasodilating purposes, in combination with a pharmacologically acceptable carrier.

9. A pharmaceutical composition which comprises a therapeutically effective amount of a compound as defined in claim 1, for analgesic purposes, in combination with a pharmacologically acceptable carrier.

10. A method for treating a subject suffering from blood circulatory insufficiency which comprises administering to the subject a pharmaceutical composition as defined in claim 8.

11. A method for treating a subject suffering from a pain which comprises administering to the subject a pharmaceutical composition as defined in claim 9.

12. A pharmaceutical composition which comprises a therapeutically effective amount of a compound as defined in claim 8, for vasodilating purposes, in combination with a pharmacologically acceptable carrier.

13. A pharmaceutical composition which comprises a therapeutically effective amount of a compound as defined in claim 8, for analgesic purposes, in combination with a pharmacologically acceptable carrier.

14. A method for treating a subject suffering from blood circulatory insufficiency which comprises administering to the subject a pharmaceutical composition as defined in claim 12.

15. A method for treating a subject suffering from a pain which comprises administering to the subject a pharmaceutical composition as defined in claim 13.

* * * * *

UNITED STATES PATENT AND TRADEMARK OFFICE
CERTIFICATE OF CORRECTION

PATENT NO. : 4 426 383
DATED : January 17, 1984
INVENTOR(S) : Hachiro SUGIMOTO et al It is certified that error appears in the above-identified patent and that said Letters Patent is hereby corrected as shown below:

On the title page, item [75], change the name of the third
    inventor to ---Sachiyuki Hamano---.

Column 49, line 55; change the lefthand portion of the formula
    to read as follows:

--- 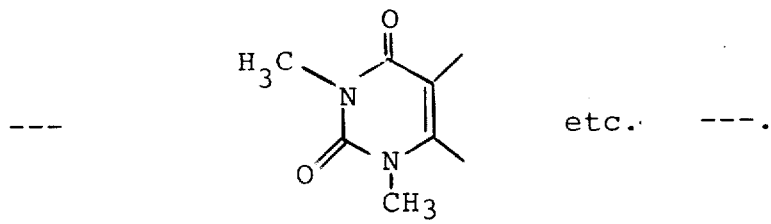 etc. ---.

Column 52, line 15; change "claim 1" to ---claim 5---.
Column 52, line 19; change "claim 1" to ---claim 5---.
Column 52, line 30; change "claim 8" to ---claim 1---.
Column 52, line 34; change "claim 8" to ---claim 1---.

Signed and Sealed this

Twenty-sixth Day of March 1985

[SEAL]

Attest:

DONALD J. QUIGG

Attesting Officer     Acting Commissioner of Patents and Trademarks